(12) United States Patent
Whitehurst et al.

(10) Patent No.: US 10,130,507 B2
(45) Date of Patent: Nov. 20, 2018

(54) DRY EYE TREATMENT DEVICE

(71) Applicants: Michael C. Whitehurst, Dallas, TX (US); Michael Lutz, Brandon, FL (US)

(72) Inventors: Michael C. Whitehurst, Dallas, TX (US); Michael Lutz, Brandon, FL (US)

( * ) Notice: Subject to any disclaimer, the term of this patent is extended or adjusted under 35 U.S.C. 154(b) by 432 days.

(21) Appl. No.: 14/451,363

(22) Filed: Aug. 4, 2014

(65) Prior Publication Data
US 2015/0320590 A1    Nov. 12, 2015

Related U.S. Application Data

(60) Provisional application No. 61/861,998, filed on Aug. 3, 2013.

(51) Int. Cl.
*A61F 7/00* (2006.01)
*A61F 7/08* (2006.01)
*A61F 9/00* (2006.01)
*A61F 7/02* (2006.01)

(52) U.S. Cl.
CPC ............ *A61F 7/007* (2013.01); *A61F 7/08* (2013.01); *A61F 9/00* (2013.01); *A61F 2007/0004* (2013.01); *A61F 2007/0075* (2013.01); *A61F 2007/0076* (2013.01); *A61F 2007/0086* (2013.01); *A61F 2007/0087* (2013.01); *A61F 2007/0093* (2013.01); *A61F 2007/0219* (2013.01)

(58) Field of Classification Search
CPC ...... A61F 2007/0075; A61F 2007/0076; A61F 2007/0004
See application file for complete search history.

(56) References Cited

U.S. PATENT DOCUMENTS

| | | | |
|---|---|---|---|
| 4,915,108 A | 4/1990 | Sun | |
| 5,097,828 A | 3/1992 | Deutsch | |
| 5,099,829 A | 3/1992 | Wu | |
| 5,169,384 A | 12/1992 | Bosniak et al. | |
| 5,871,526 A * | 2/1999 | Gibbs | A61F 7/02 165/46 |

(Continued)

FOREIGN PATENT DOCUMENTS

| | | |
|---|---|---|
| EP | 3177243 | 3/2018 |
| WO | WO2016022596 A1 | 2/2016 |

OTHER PUBLICATIONS

International Search Report and Written Opinion, WO2016022596, dated Dec. 22, 2015.

(Continued)

*Primary Examiner* — Joseph Stoklosa
*Assistant Examiner* — Adam Avigan
(74) *Attorney, Agent, or Firm* — Law Office of Sam Sokhansanj PLLC

(57) ABSTRACT

A dry eye treatment device and method of use are disclosed for applying heat to the exterior surface of an eyelid to treat dry eye symptoms which can be caused by meibomian gland dysfunction (MGD). More specifically, a user operable main unit and hand piece are provided that allow the user to heat his/her or another patient's eyelids to a desired temperature, which can effectively and efficiently raise the temperature at the meibomian glands sufficient to melt, loosen, or soften occlusions or obstructions in the meibomian glands, thereby restoring natural secretory function to the meibomian glands.

20 Claims, 10 Drawing Sheets

(56) References Cited

U.S. PATENT DOCUMENTS

| | | |
|---|---|---|
| 5,964,723 A | 10/1999 | Augustine |
| 6,024,095 A | 2/2000 | Stanley, III |
| 6,273,886 B1 | 8/2001 | Edwards et al. |
| 6,455,583 B1 | 9/2002 | Pflugfelder et al. |
| 6,679,908 B2 | 1/2004 | Shimizu |
| 6,840,954 B2 | 1/2005 | Dietz |
| 6,882,885 B2 | 4/2005 | Levy, Jr. et al. |
| 6,886,933 B2 | 5/2005 | Schwebel |
| 7,004,942 B2 | 2/2006 | Laird et al. |
| 7,069,084 B2 | 6/2006 | Yee |
| 7,108,694 B2 | 9/2006 | Miura et al. |
| 7,122,013 B2 | 10/2006 | Liu |
| 7,195,603 B2 | 3/2007 | Yamazaki et al. |
| 7,211,070 B2 | 5/2007 | Soroudi |
| 7,231,922 B2 | 6/2007 | Davison et al. |
| 7,357,500 B2 | 4/2008 | Schwebel |
| 7,513,893 B2 | 4/2009 | Soroudi |
| 7,758,534 B2 | 7/2010 | Pearson |
| 7,976,573 B2 | 7/2011 | Korb et al. |
| 7,981,095 B2 * | 7/2011 | Grenon ................ A61F 9/0008 604/289 |
| 7,981,145 B2 | 7/2011 | Korb et al. |
| 7,981,146 B2 | 7/2011 | Korb et al. |
| 7,981,147 B2 | 7/2011 | Korb et al. |
| 8,007,524 B2 | 8/2011 | Korb et al. |
| 8,025,689 B2 | 9/2011 | Korb et al. |
| 8,617,229 B2 | 12/2013 | Korb et al. |
| 8,915,253 B2 | 12/2014 | Grenon et al. |
| 9,039,718 B2 | 5/2015 | Rynerson |
| 9,719,977 B2 | 8/2017 | Korb et al. |
| 2005/0288748 A1 | 12/2005 | Li et al. |
| 2007/0016254 A1 * | 1/2007 | Grenon ............... A61F 9/00772 607/1 |
| 2007/0060988 A1 * | 3/2007 | Grenon ................. A61F 9/00 607/96 |
| 2007/0081848 A1 * | 4/2007 | Ramet ................. A45D 34/04 401/11 |
| 2007/0286665 A1 * | 12/2007 | Bouix ................. A45D 40/267 401/1 |
| 2008/0109053 A1 | 5/2008 | Grenon et al. |
| 2008/0114423 A1 * | 5/2008 | Grenon ................. A61F 7/12 607/96 |
| 2008/0148461 A1 | 6/2008 | Guyuron et al. |
| 2008/0300529 A1 | 12/2008 | Reinstein |
| 2009/0221943 A1 * | 9/2009 | Burbank ............... A61H 1/008 601/46 |
| 2012/0065556 A1 | 3/2012 | Smith et al. |
| 2013/0110101 A1 | 5/2013 | Van Valen et al. |
| 2013/0211395 A1 * | 8/2013 | Schwartz ........... A61F 9/00745 606/28 |
| 2014/0142055 A1 | 5/2014 | Hosseini et al. |
| 2014/0142663 A1 | 5/2014 | Van Valen |
| 2015/0032192 A1 | 1/2015 | Pezzi |
| 2015/0100001 A1 * | 4/2015 | Bujak ................... A61F 9/007 601/2 |

OTHER PUBLICATIONS

European Search Report for EP App. No. 15830214/EP3177243 (Whitehurst et al.), dated Feb. 8, 2018, 7 pp. total.

* cited by examiner

DRY EYE TREATMENT DEVICE

CROSS REFERENCE TO RELATED APPLICATIONS

This application claims the benefit of U.S. Provisional Application No. 61/861,998 filed on Aug. 3, 2013, which is incorporated herein by reference in its entirety.

FIELD OF THE INVENTION

The present invention relates generally to the field of ophthalmology. More particularly, the present invention relates to treatment of meibomian gland dysfunction (MGD), which may be either responsible for or be a contributing factor to a patient suffering from a "dry eye" condition.

BACKGROUND OF INVENTION

This section is intended to introduce the reader to aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Dry eye or irritated eye symptoms typically result from an insufficiently lubricated ocular surface of the eye, which can be caused by a change or reduction in the composition of a lipid component of a tear film coating of the eye. These changes in the lipid layer are often the result of obstructive meibomian gland dysfunction (MGD), a form of posterior blepharitis that results in changes to the local eyelid margin. In particular, obstruction of the meibomian glands may decrease delivery of meibomian gland secretions, which include various oil and lipid components typically secreted from the meibomiam glands upon blinking.

The aforementioned MGD may arise from one or more meibomiam gland ducts becoming plugged or partially plugged with meibomiam gland products such as lipids and oils. Due to various factors, these lipids and oils may solidify thereby plugging the gland ducts. As a result of the plugging and solidification, sufficient meibomiam oils and lipids may not be expressed onto the tear film. In addition, secretory product and bacteria may also build up within the gland.

Hence, what is needed is an effective and easy to use device capable of unplugging severely plugged meibomiam gland ducts of the eye thereby relieving a patient of MGD. The dry eye treatment device of the present invention addresses one or more of the concerns set forth above.

BRIEF SUMMARY OF THE INVENTION

In one aspect of the present invention, a dry eye treatment device and method of use are disclosed for applying heat to the exterior surface of the eyelid to treat dry eye caused by meibomian gland dysfunction (MGD). More specifically, a user operable main unit and hand piece are provided that allow the user to heat his/her or another user/patient's eyelids to a desired temperature, which can effectively and efficiently raise the temperature at the meibomian glands to a temperature sufficient to melt, loosen, or soften more serious occlusions or obstructions in the meibomian glands, and restore natural secretory function to obstructed glands. Further, the eye treatment device of the present invention is user programmable, simple to operate and use, cost effective to manufacture, and can effectively treat MGD without additional surgical operations, devices, or pharmaceutical drugs.

In another aspect of the present invention, an eye treatment device is provided having a heating element disposed within a hand-held unit, and wherein the heating element is coupled to an eyelid applicator. The eyelid applicator is configured to apply heat to an exterior surface of one or more eyelids. In addition, a controller can be in communication with the heating element, wherein the controller is configured to regulate a temperature of the heating element. In addition, the eyelid applicator can further include a partially curved surface. In addition, the heating element and eyelid applicator are part of a hand-held unit. Further, the controller can be disposed within a main unit, wherein the main unit is coupled to the hand-hand unit. Also, the eyelid applicator can be further coupled to a thermal transfer rod, wherein the rod is further coupled to the heating element. The thermal transfer rod can be at least partially bent. Further, the heating element is a Peltier device.

In another aspect of the present invention, an eye treatment device is provided having a hand-held unit having a heating element, wherein the heating element is further coupled to an end piece, and wherein the end piece is configured to transfer heat to one or more eyelids. The device can further include a main stationary unit, wherein the main unit communicates with the hand-held unit. Here, the main unit can regulate a temperature of the heating element. In addition, the main unit can further include a user interface display, wherein the user interface display is configured to control operation of the hand-held unit.

In another aspect of the present invention, a method of treating an eye with an eye treatment device is provided. The method includes heating an end piece of a hand-held unit, positioning the heated end piece on an exterior surface of an eyelid, and moving the end piece on the exterior surface of the eyelid. Here, the end piece is heated by a heating element disposed within the hand hand-held unit. The method can further include applying a substance to the exterior surface of the eyelid, wherein the substance is an ultrasound gel. In addition, moving the end piece on the exterior surface of the eyelid promotes meibomian gland function of the eyelid.

The above summary is not intended to describe each and every disclosed embodiment or every implementation of the disclosure. The Description that follows more particularly exemplifies the various illustrative embodiments.

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following detailed description of various embodiments in connection with the accompanying drawings, in which.

DETAILED DESCRIPTION

In the Brief Summary of the present disclosure above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The embodiments set forth below represent the necessary information to enable those skilled in the art to practice the invention and illustrate the best mode of practicing the invention. In addition, the invention does not require that all the advantageous features and all the advantages need to be incorporated into every embodiment of the invention.

Phrases and terms similar to "software", "application", "algorithm", and "firmware" may include any non-transitory computer readable medium storing thereon a program, which when executed by a computer, causes the computer to perform a method or function.

Phrases and terms similar to "network" may include one or more data links that enable the transport of electronic data between computer systems and/or modules. When information is transferred or provided over a network or another communications connection (either hardwired, wireless, or a combination of hardwired or wireless) to a computer, the computer uses that connection as a computer-readable medium. Thus, by way of example, and not limitation, computer-readable media can also comprise a network or data links which can be used to carry or store desired program code in the form of computer-executable instructions or data structures and which can be accessed by a general purpose or special purpose computer.

In one aspect of the present invention, a device and method are disclosed for applying heat to the exterior surface of one or more eyelids to treat dry eye caused by meibomian gland dysfunction (MGD). Applying heat to the exterior of the eyelid can effectively and efficiently raise the temperature at the meibomian glands to a temperature sufficient to melt, loosen, or soften more serious occlusions or obstructions in the meibomian glands. The occlusions or obstructions can then be physically expressed to improve sebum flow from the meibomian glands to reduce evaporation of the aqueous layer.

Figure 1:
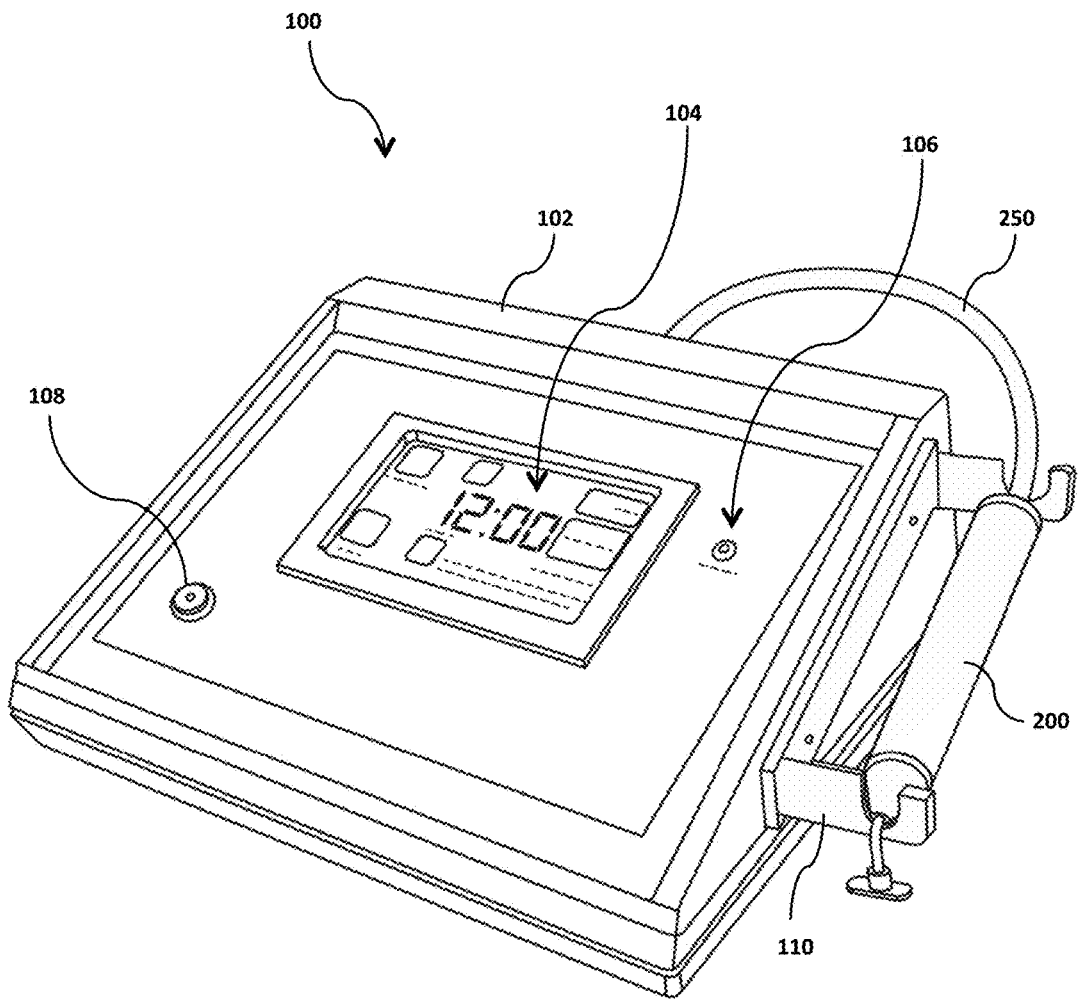
FIG. 1 illustrates a perspective view of an embodiment for the eye treatment device of the present invention.
Figure 2:
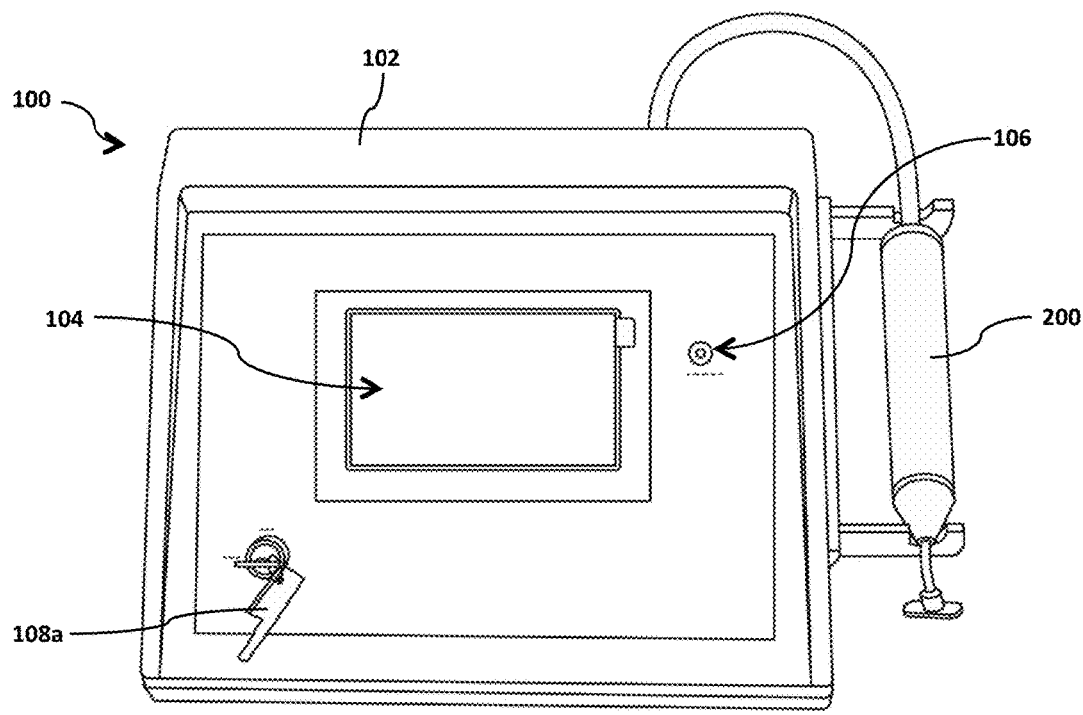
FIG. 2 illustrates a top view of the eye treatment device for the embodiment of FIG. 1.
Figure 3:
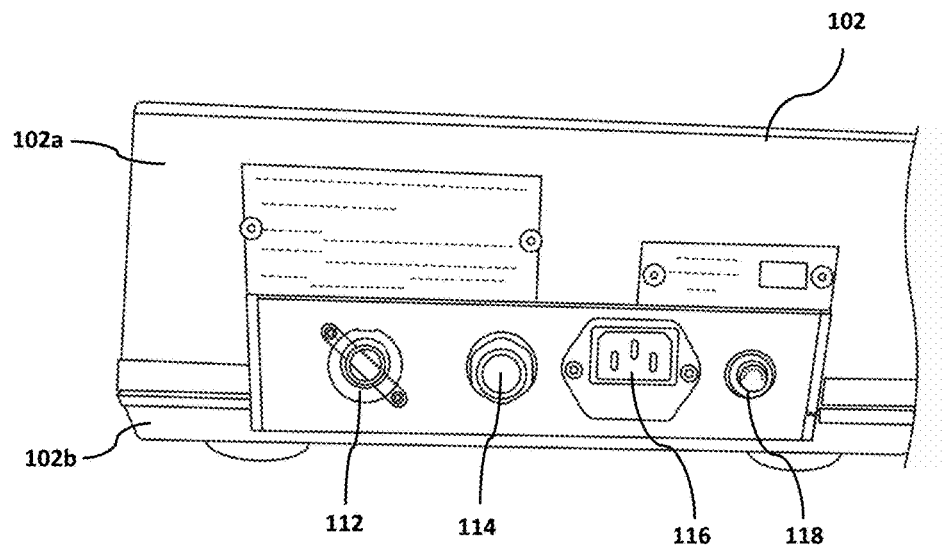
FIG. 3 illustrates a rear view of an embodiment for the eye treatment device of the present invention.

FIG. 1-2 illustrates a perspective view and top view of one embodiment for the dry eye treatment device of the present invention. Specifically, the dry eye treatment device 100 includes a controller or main unit 102 having a housing or casing, and wherein the main unit 102 is connected to a hand piece, or hand-held unit applicator 200 via electrical cord, cable, or tubing 250. Here, main unit 102 includes a user interface display 104, a key lock 108 with key, a light indicator 106, and holder arms 110 for holding or docking hand piece 200. Referring, to FIG. 3, main unit 102 includes a top half housing 102a and a bottom half housing 102b coupled to each other. In addition, main unit 102 includes an electrical outlet socket 116 for powering the eye treatment device 100, wherein the outlet can be connected to any type of standard electrical wall outlet, such as 110V, 220V, 120V, or 240V outlets. Alternatively, the main unit and hand piece can be powered via one or more batteries, wherein each of main unit 102 and hand piece 200 can include battery packs. Further, the main unit is outfitted with a cooling fan 112 for cooling the internal components of the housing. In addition, outlet 114 connects hand piece 200 with main unit 102 via cord 250. Outlet 118 can be a factory service port for running diagnostic testing, programming, or upgrading, changing, or modifying the software, firmware, applications, hardware, and internal components for the eye treatment device 100.

Figure 4:
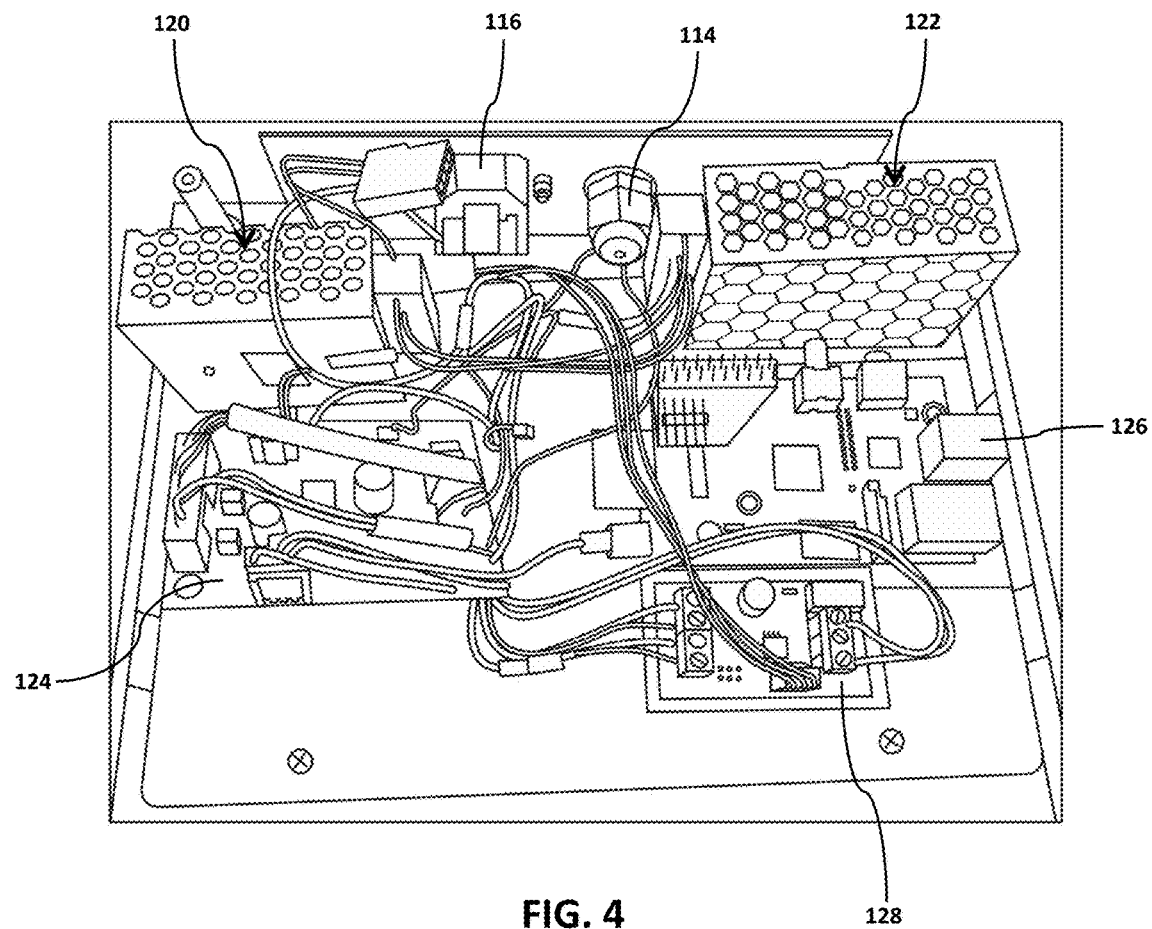
FIG. 4 illustrates a top view for an embodiment of the internal components for the eye treatment device of the present invention.

FIG. 4 illustrates a top view for the internal hardware components for the man unit 102 of the eye treatment device 100. More specifically, here top half casing 102a has been removed. Here, main unit 102 generally includes I/O board 124, thermal controller 128, central processing unit (CPU) 126, 3.3 v LVPS power supply 122, and 12 v LVPS power supply 120. Here, the aforementioned components can include one or more processors adapted to operate in accordance with one or more algorithms that can control or at least partially control one or more components of the device as further shown in FIG. 5, including but not limited to display 104, heating and cooling elements, sensors, thermocouples, timers, and hand piece applicator of the eye treatment device, among others.

Figure 5:
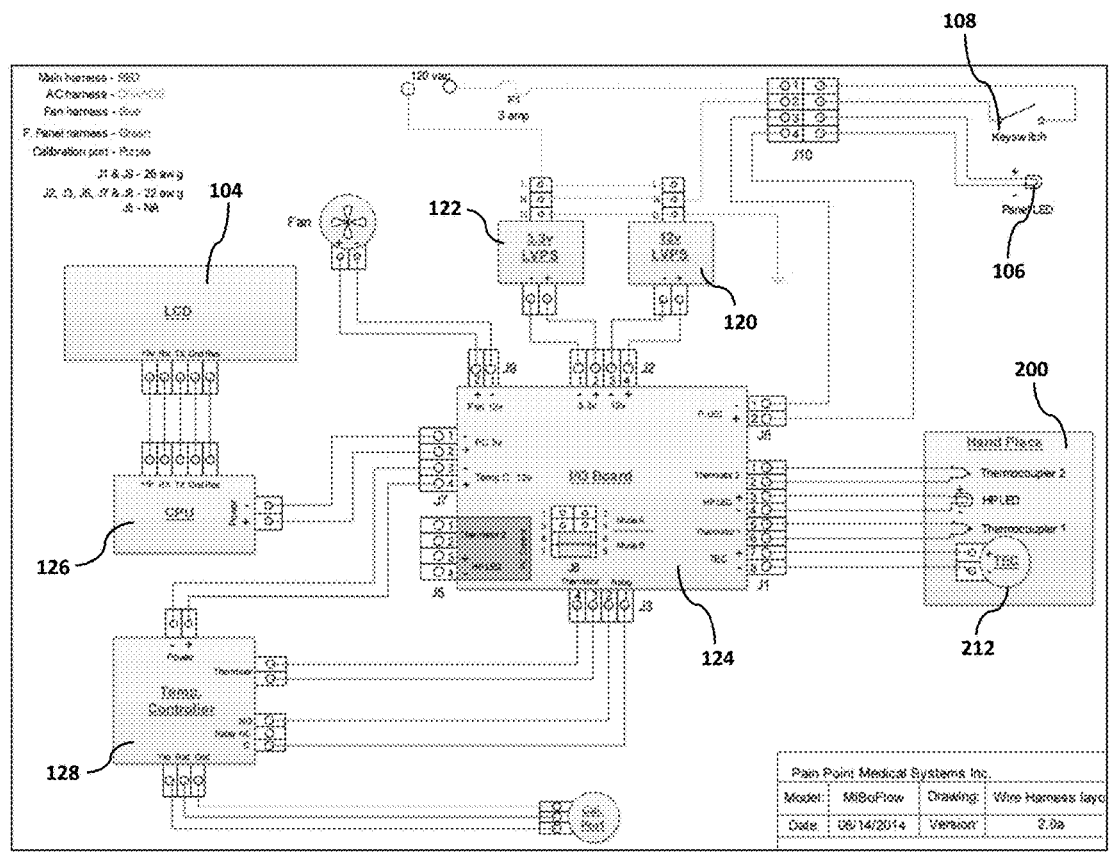
FIG. 5 illustrates a schematic electrical diagram for an embodiment of the eye treatment device of the present invention.

FIG. 5 illustrates a detailed electrical schematic diagram for the communication and connections between the components of the eye treatment device. More specifically, main controller or I/O board 124 is shown communicating with CPU 126, which communicates and controls and operates display 104. The display 104 can be a touchscreen display that function's as both a display and keypad or user input device. In some instances, a display can include or may be a liquid crystal display (LCD), high performance addressing display (HPA), thin film transistor display (TFT), light emitting diode (LED), organic light emitting diode (OLED), or an image (or moving image) projector. In the current embodiment, the touch screen panel can be adapted to solicit values for a number of operating parameters and/or to receive said values. In addition, the display screen may provide haptic feedback to a user.

Still referring to FIG. 5, I/O board 124 further communicates with temperature controller 128 connected to a calibration port. I/O board 124 further communicates with the components of hand piece 200, namely, at least two thermocouples (thermistors), LED light indicator, and Peltier device or TEC thermoelectric device 212. Here, in one embodiment, main unit 102, and other internal components. The I/O board 124 can be powered by a 12 v LVPS (low voltage power supply) unit 124 and handpiece 200 (including its internal components) can be powered by a 3 v LVPS power supply. However, it is contemplated within the scope of the invention that any type or any number of power supplies may be used to power any one or more components of eye treatment device.

Figure 6:
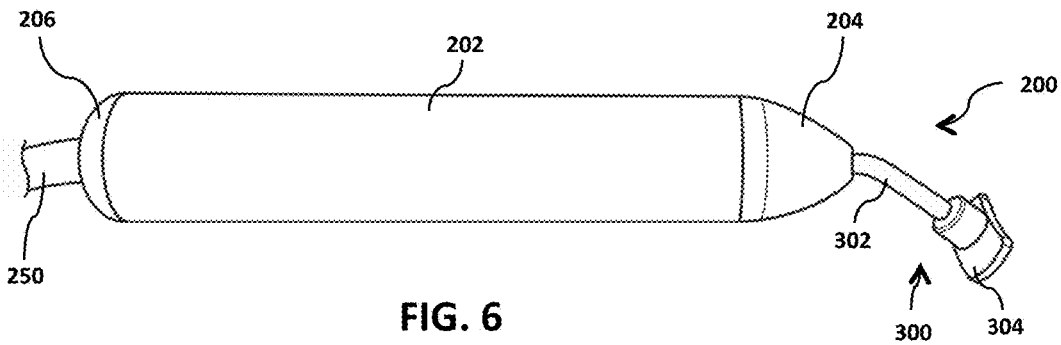
FIG. 6 illustrates a side perspective view of an embodiment for a hand piece or applicator of the eye treatment device of the present invention.
Figure 16:
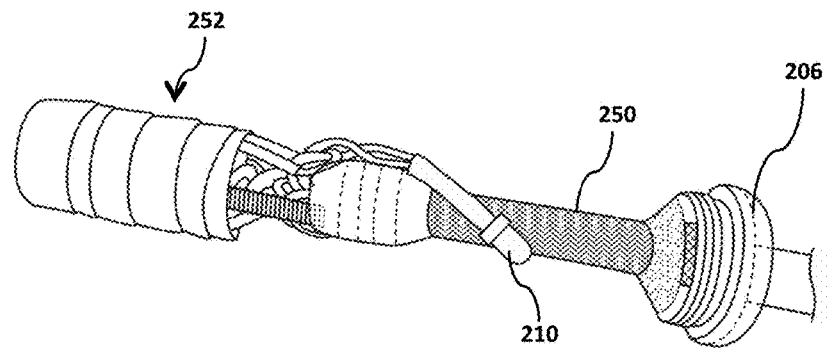
FIG. 16 illustrates a perspective view of the internal components for the hand piece or applicator of the eye treatment device of the present invention.
Figure 17:
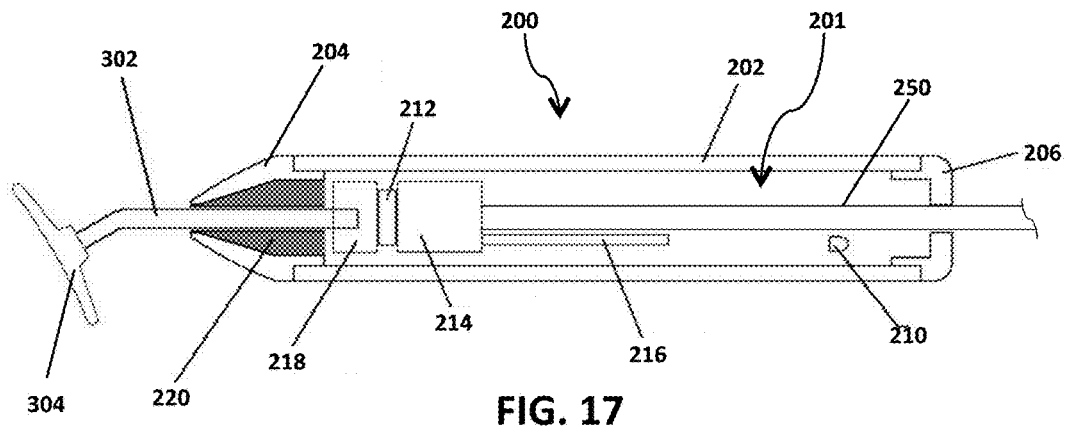
FIG. 17 illustrates a cross-sectional side view of the hand piece and applicator for the eye treatment device of the present invention.
Figure 18:
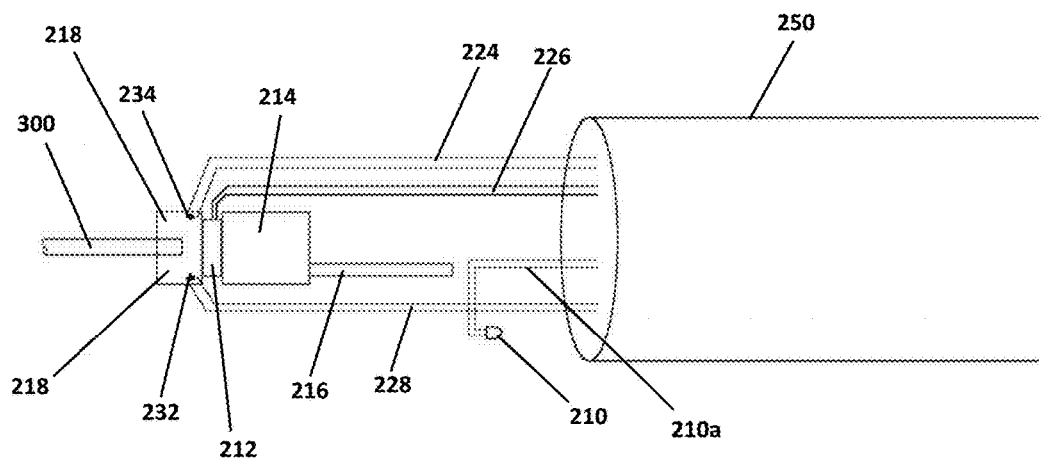
FIG. 18 illustrates another close-up cross-sectional side view of the hand piece for the eye treatment device of the present invention.

FIG. 6 illustrates an embodiment for the hand piece 200 of the eye treatment device. Here, Specifically, hand piece 200 includes an eyelid applicator or end piece 300 that includes an eyelid contact component 304 that is coupled to or integrated with a thermal transfer rod 302 and wherein the transfer rod 302 is secured and engaged within bullet shaped distal end piece or cap 204, and further wherein end piece 204 further secures rod 302. Here, end piece 204 can be fixed or removable and can be threadably engaged with and connected to main cylindrical or tubular body component 202, wherein body 202 at least partially houses the internal components of hand piece 200. Hand piece 200 further includes a removable or fixed end cap or base 206 coupled to main body 202. End cap 206 includes an annular opening for receiving tubing 250. Here, in one embodiment, end cap can be a clear or colored transparent or semi-transparent component that can be illuminated via a light indicator 210 (FIGS. 16-18). In another embodiment, the entire hand piece can be a clear or colored transparent or semi-transparent material that can be illuminated. In other embodiments, any one or more parts of hand piece can be a solid or opaque components. In one embodiment, one or more of the aforementioned parts for hand piece 200 can be made of one or more metals, aluminum, silver, stainless steel, plastic, acrylics, copper, heat resistant material, and heat absorbing material, among others. In further embodiments, any one or more components 202, 204, 206, 300, 302, and 304 can either be independent parts or integrated with one or more other parts, or all parts 202, 204, 306, 300, 302, and 304 can be one unitary piece. Alternatively, part 300 (collectively 302 and 304) can be the only removable and interchangeable parts of hand piece 200. In such an embodiment, parts 302 and 304 are integrated and fixed to each other. However, it is contemplated within the scope of the invention that either one or more of parts 302 and 304, individually or combined, can be interchangeable.

Figure 7:
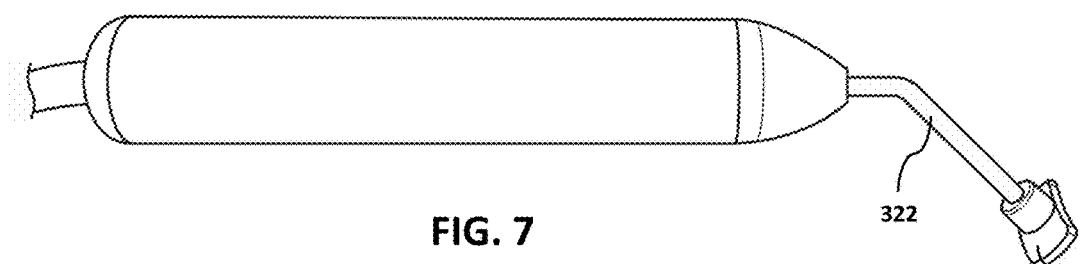
FIG. 7 illustrates a side perspective view for another embodiment for a hand piece or applicator of the eye treatment device of the present invention.
Figure 8:
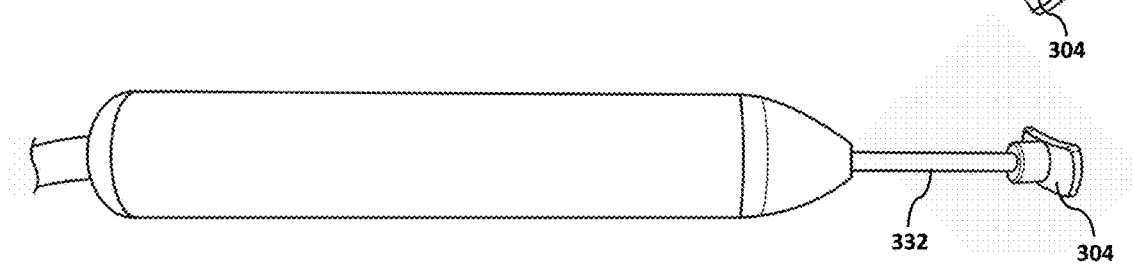
FIG. 8 illustrates a side perspective view for another embodiment for a hand piece or applicator of the eye treatment device of the present invention.
Figure 9:
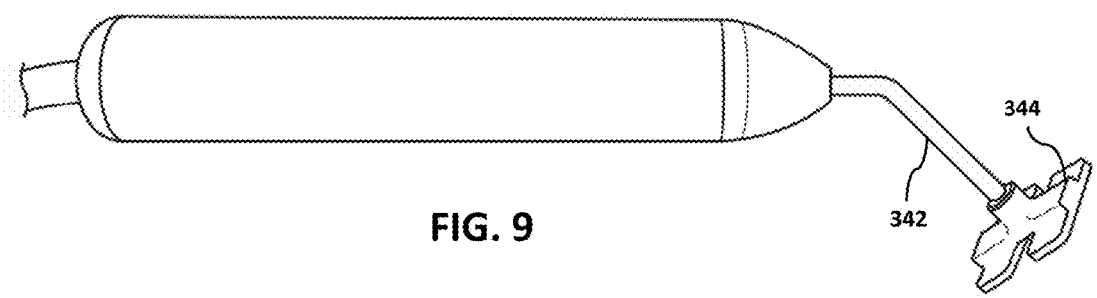
FIG. 9 illustrates a side perspective view for another embodiment for a hand piece or application of the eye treatment device of the present invention.
Figure 10:
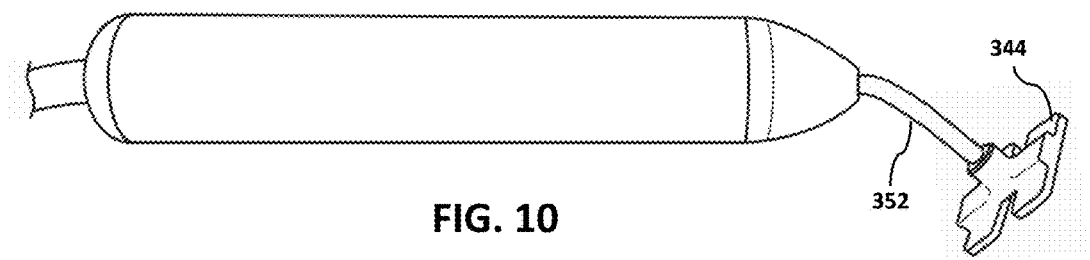
FIG. 10 illustrates a perspective side view for another embodiment for a hand piece or applicator of the eye treatment device of the present invention.
Figure 11:
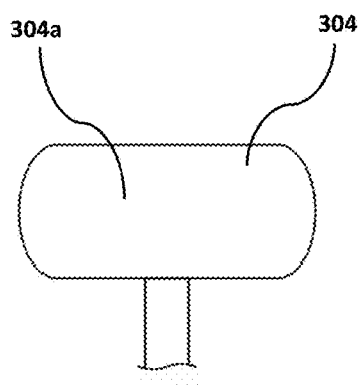
FIG. 11 illustrates a front view for an embodiment for an eye contact part for the hand piece of the eye treatment device of the present invention.
Figure 13:
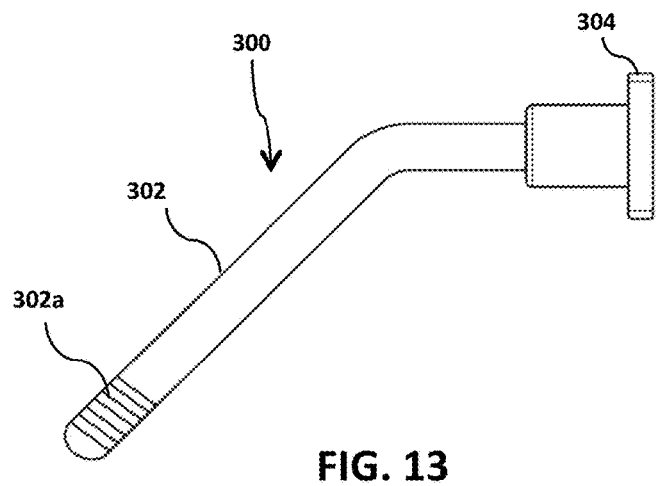
FIG. 13 illustrates a side view for the eye contact part and thermal transfer rod of FIG. 11.
Figure 12:
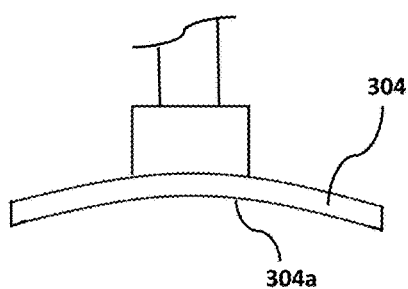
FIG. 12 illustrates a top view for the eye contact component of FIG. 11.
Figure 14:
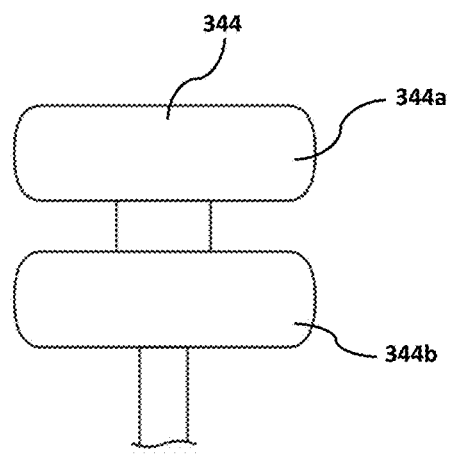
FIG. 14 illustrates a front view for another embodiment for a double tip eye contact part for the hand piece of the eye treatment device of the present invention.

FIGS. 7-10 illustrate various embodiments for the end piece or eyelid applicator having an eyelid contact component configurations and thermal transfer rod orientations for the hand piece 200 of the eye treatment device. Specifically, FIG. 7 illustrates a thermal transfer rod 322 having a slightly or partially bent configuration, preferably a 30-degree angle with respect to a horizontal plane. The bent configuration of the rod allows for a more natural position of the hand-held unit 200 by a user during a treatment session. However, it is contemplated within the scope of the invention that the bend in rod 322 or any of rods 302, 332, 342, and 352 can be anywhere from 1-degree up to and include 90-degrees. Still referring to FIG. 7, rod 322 is shown further coupled to or integrated with the at least partially arched or concave single tip eyelid contact piece 304 (FIGS. 11-13). FIG. 8 illustrates a thermal transfer rod 332 in a straight configuration or parallel with respect to a horizontal plane, wherein rod 332 is further coupled to or integrated with eyelid contact piece 304. FIG. 9 illustrates an embodiment for a slightly or at least partially bent thermal transfer rod 342 coupled to or integrated with an at least partially arched or concave surface double tip eyelid contact piece 344 (FIG. 14). FIG. 10 illustrates another embodiment for a slight curved or at least partially curved or bent thermal transfer rod 352 coupled to or integrated with an at least partially concave surface double tip eyelid contact piece 344 (FIG. 14). Here, eyelid applicator 300, including any of parts 302, 304, 322, 332, 342, and 344 can be rigid components; however, it is contemplated within the scope of the invention that they can also be flexible.

FIGS. 11-13 illustrates various views for an embodiment of the end piece 300 and eyelid contact piece 304. Here, piece 300 is generally shown having a "T" shaped configuration that allows it make contact with the upper or lower human eyelid. Eyelid contact tip piece 304 is shown as a single contact tip component having a partially or slightly concave, arched, or curved outer surface 304a. Here, curvilinear, curved, arched, or concave surface 304a is configured as such to accommodate the convex shape of a closed human upper or lower eyelid in order to make partial or substantial contact with the exterior surface of the closed upper or lower eyelids. Rod 302 includes a threaded end that allows piece 300 (rod 302 and tip 304) to be removable and interchangeable with hand piece 200. Here, the threaded end of rod 302 can be threaded into cap 204. It is contemplated within the scope of the invention that tip 304 may also be coupled to or integrated with any of the aforementioned rods 302, 322, or 332 of the eye treatment apparatus.

Figure 15:
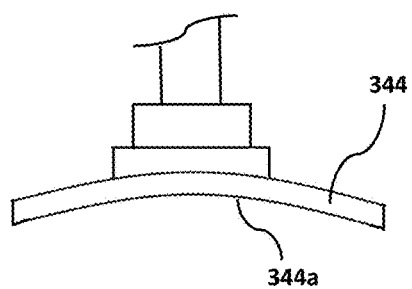
FIG. 15 illustrates a top view for the embodiment of FIG. 14.

FIGS. 14-15 illustrate various views for another embodiment for end piece 300 and double tip eyelid contact piece 344. Here, piece 344 is generally shown having a "T" shaped configuration that allows it make contact with the upper or lower human eyelid. Eyelid contact tip piece 344 is shown as a dual or double contact tip component wherein each tip has a first and second outer surfaces 344a and 344b having a partially or slightly concave outer surface. Here, concave or curved surfaces 344a and 344b are configured as such to accommodate the convex shape of a human upper or lower eyelid in order to make partial or substantial contact with the exterior surface of the closed upper or lower eyelids. Rod 302 includes a threaded end 302a that allows piece 300 (rod 302 and tip 304) to be removable and interchangeable with hand piece 200. In one embodiment, the threaded end can engage cap 204 and/or heat block 218. It is contemplated within the scope of the invention that tip 304 may also be coupled to or integrated with any of the aforementioned rods 302, 322, or 332 of the eye treatment apparatus.

FIG. 16 illustrates some of the interior components of hand piece 200 with the main body or sleeve 202, cap 204, and eyelid applicator 300 removed. Here, fiberglass wrap 252 securely encloses parts 212, 214, and 218 (FIG. 17) of the hand piece. Also shown is LED or light source 210 that allows end cap 206 to be illuminated during operation for the eye treatment device, which will later be described in detail.

FIG. 17 illustrates a partial cross-sectional side view for hand piece 200. Specifically, hand piece 200 includes a Peltier element, thermoelectric cooling (TEC), heating element, or Peltier device 212, which is generally a solid-state active heat pump that transfers heat from one side of the device to the other, with consumption of electrical energy, depending on the direction of the current. In the current embodiment, Peltier device 212 can operate as a generator wherein one side of the device is heated to a temperature greater than the other side, and as a result, a difference in voltage is built up between the two sides. Peltier device 212 can achieve a thermoelectric effect, Peltier effect, Seabeck effect, or Thomson effect. For example, in one embodiment, the Peltier device of the hand piece can be comprised of both a cylindrical or circular hot side and cylindrical or circular cold side adjacent to each other and connected to each other via two thermo electrical legs. However, It is contemplated within the scope of the invention that the Peltier device 212 can take any shape, dimension, or configuration, including but not limited to square, plates, rectangular, oval, ellipsoid, or circular.

Still referring to FIG. 17, Peltier device 212 is further connected to a cold block 214 and copper heat block 218. Heat block 218 is further connected to thermal transfer rod 302, which is further connected to eyelid contact piece 304. Heat block 218 can further amplify the heating effect on transfer rod 302, whereas cold block 214 can assist in dissipating heat from Peltier 212 when in heating mode. Here, Peltier 212 operates to heat eyelid contact applicator piece 304. In addition, a thermal compound 220 or a high "R" insulation foam is provided to insulate the shaft, end piece 204, and main body 202 of the hand piece 200. Here, the thermal compound can be distributed through the interior space 201 of hand piece 200. In addition, a wire support bar 216 is provided for supporting and securing various wiring.

Referring now to FIG. 17 and FIG. 18, cable tubing or cord 250 includes a plurality of wiring for powering, sensing, and operating a plurality of internal components of hand piece. Here, wiring within cord 250 is further connected to main unit 102, and more specifically the I/O board 124 (FIG. 5) which at least partially controls operation for Peltier 212, thermocouples 234 and 232, and LED light source 210, among others. In the current embodiment, wiring 224, 226, 228, and 210a are disposed within cord tubing 250 and further connected to main unit 102. Specifically, wiring 226 is configured to power, operate, and heat Peltier 212. Heat block 218 of Pelter 212 is further connected to and/or integrated with thermocouples or thermistors 232 and 234 on opposing sides of heat block 218. Here, thermocouples 232 and 234 communicate and transfer temperature data via wiring 228 and 224, respectively, back to main unit 102 and more specifically I/O board 124 (FIG. 5). Here, thermocouples 232 and 234 operate to regulate temperature for Peltier 212 and further error checking each other. More specifically, Peltier 212 is pre-programmed (or set by a user) to operate at a certain temperature within a temperature range and thermocouples 232 and 234 operate to regulate this temperature via communicating with the temperature controller 128, I/O board 124, and controller/main unit 102. For example, temperature controller 128 can regulate the temperature of Peltier 212 at a constant pre-defined temperature. In addition, wiring 210a powers and operates LED light source 210, wherein source 210 can further illuminate base 206. For example, in one embodiment, light source 210 can be in a blinking or flashing mode while Peltier 212 is being heated to achieve a temperature range or set or pre-programmed temperature, such as 108-degrees Fahrenheit. When Peltier 212 reaches the pre-programmed temperature, then light source 210 can switch to a steady or constant illumination mode (non-blinking).

One or more embodiments for operation of the eye treatment device 100, hand piece 200, and more specifically Peltier 212 will now be described in detail. The present invention is not limited to the following embodiments for a method of use. In addition, the following method of use and steps can be performed in any order and may include some steps and omit others, or include steps not otherwise disclosed. Peltier device 212 can be regulated to operate within various temperature ranges. In this regard, an embodiment of the eye treatment device is to apply heat via the hand piece 200 to the exterior surface of the closed upper or lower eyelid of a user via hand piece 200 to treat MGD, meibomian glands, dry eyes and/or stimulate tears, gland muscles, expression of fluids, expression of tear film component, among others, as illustrated in FIGS. 23-24.

Figure 19:
FIG. 19 illustrates a top view for a home screen display for an embodiment of the eye treatment device of the present invention.

In one embodiment for a method of use of the dry eye treatment device of the present invention, a user or healthcare professional can un-lock the treatment device 100 via key 108a within lock 108 (FIG. 1-2). Once unlocked, the main unit 102 can automatically turn on or the user can manually turn on the device. The user can then be presented with a home screen via user interface display 104, as illustrated in FIG. 19. Here, the device 100 and can begin warming up main unit 102 and heating Peltier 212 of hand piece 200. The home screen display can further display a timer 1400 for the user to observe until Peltier 212 (and ultimately parts 300, 302, 304) of hand piece 200 is fully heated. In the current embodiment, warm up time can be approximately five minutes; in other embodiments, the warm-up time can be anywhere from 5 seconds up to and including 15 minutes. Here, once the timer reaches zero, the user can select start icon 1402 and the display screen can move to the user interface treatment or session screen illustrated in FIG. 20. Alternatively, the display can automatically move to a treatment or session screen in FIG. 20 without additional user input. In addition, light source or light indicator 106 (FIG. 1) can be in a steady (on) illumination mode when the unit is warming up and in a blinking (on/off) mode when the unit has fully heated hand piece 200 and is ready for operation, vice versa. For example, during a treatment session, there may be a temperature drop at the eyelid contact applicator 300 where the hand piece may briefly go into warming up mode (blinking light from 106) and then resume a fully heated mode (steady illumination from 106), or vice versa. In other embodiments, light indicator 106 can be in one color (i.e. red) while the device is warming up and switch to another color (i.e. green) when the device is ready to operate.

Figure 20:
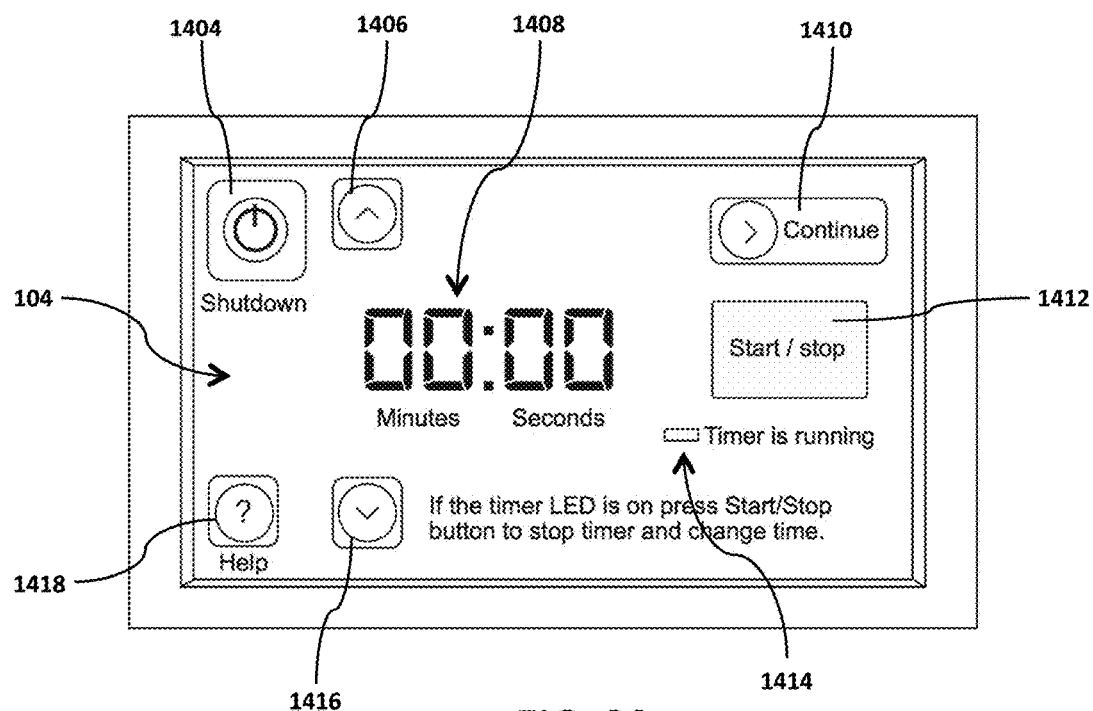
FIGS. 20-22 illustrates a top view for an operational screen display for an embodiment of the eye treatment device of the present invention.
Figure 21:

Referring to FIG. 20, the user can be provided with the option to set a timer 1408 for how long he or she wants to operate the eye treatment device for a given session. Timer 1408 can be pre-programmed or set by the user by selecting upper icon 1406 for increasing time and lower icon 1416 for decreasing the time, and a timer is running indicator 1414. Here, during a treatment session (or prior to beginning a session), a user may go back and forth between various screens. For example, Help icon 1418 will allow the user to view and review various help, procedure, safety, tips, and guidance for operating the user treatment device. A global continue icon 1410 allows the user to go back to main treatment screen in FIG. 20 without interrupting operation of the timer 1408 (if a treatment session has already been initiated). Here, once the user has set the timer for a particular session, he or she can select the Start/Stop icon 1412 to start the timer which will direct the user to user interface display screen in FIG. 21, and the user can begin treating one or more eyelids of a patient with hand piece 200 (FIG. 23-24), which will be described in detail later. A shutdown icon 1404 is also provided.

Figure 23:
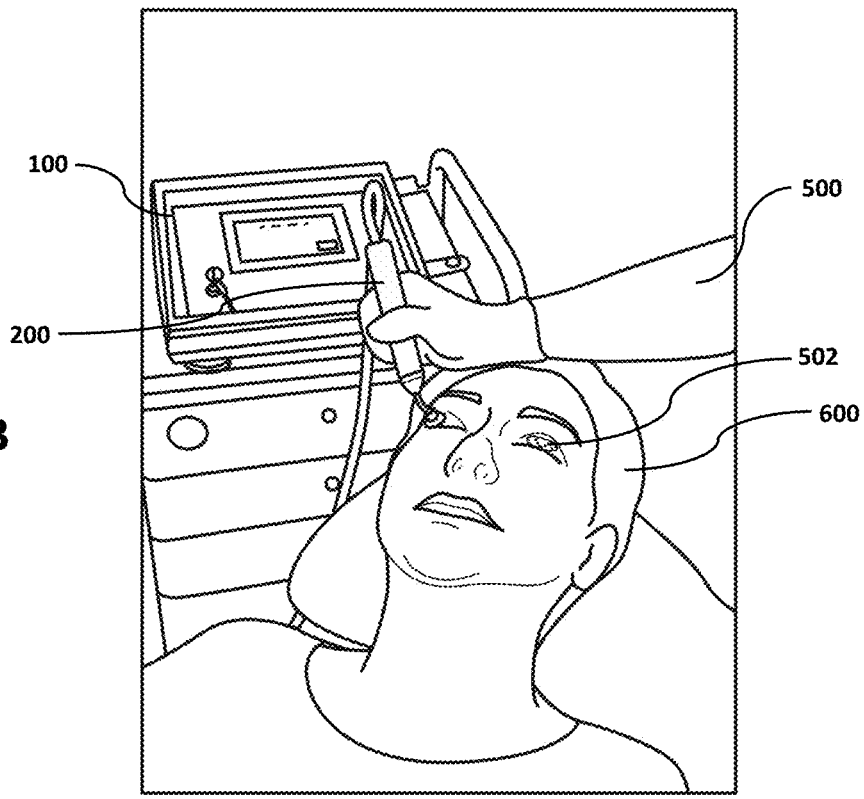
FIG. 23 illustrates a perspective view of a patient and user for a method of use of the eye treatment device of the present invention.
Figure 24:
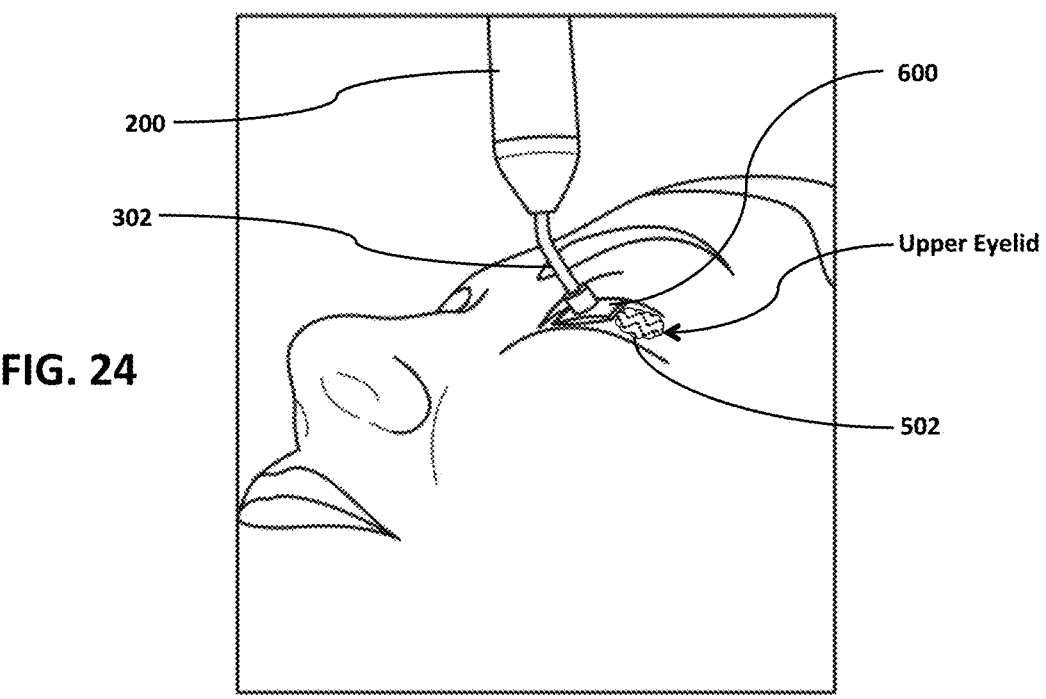
FIG. 24 illustrates a close-up perspective view of the patient's eyelid and eyelid contact part for the embodiment of FIG. 23.

In one embodiment for a method of use for the eye treatment device, as shown in FIGS. 23-24, a gel 502 or a suitable chemical, cream, liquid, or substance for transferring heat can be applied to the outer exterior surface of upper eyelids of patient 600 prior to beginning a treatment session. Here, the gel or substance can be an ultrasound gel. The gel 502 can be applied prior to even turning on the device 100 or during the warm up session (FIG. 19). More specifically, the eyelids can be coated with the ultrasound gel prior to bringing the eyelid contact piece 304 in direct contact the exterior eyelid of the patient 600. In advantage of applying the ultrasound gel is that the heat dissipated by component eyelid contact component 304 can penetrate the eyelid and meibomian glands much deeper than without it, thereby improving the ability of the eye treatment device in treating MGD, meibomian glands, dry eyes and/or stimulate tears, gland muscles, expression of fluids, expression of tear film component, among others. The ultrasound gel can comprise of the ingredients propylene glycol, glycerin, phenoxyethanol, and a colorant. Furthermore, a darker colored ultrasound gel (such as black) or a clear ultrasound gel can also be used, wherein the darker colored ultrasound gel can allow the heat to penetrate through the outer eyelids much deeper than clear or light colored ultrasound gels. In other embodiments, no gel or liquid may be used, and the eyelid applicator can be used and operated on the outer eyelids without additional substances applied to the eyelids.

Once, the gel has been applied to the eyelid and the timer 1408 has been set and started, the user 500 can gently place the outer surface of eyelid contact piece 304 into direct contact with the closed exterior surface of the user's eyelid, such as the upper eyelid. Here, depending on the application and patient, the piece 304 of hand piece 200 can either be gently or at least partially moved across the outer surface of the eyelid, in addition, the user can apply a gentle pressure, force, or a massaging action while moving piece 304 around the exterior surface of the outer upper or lower eyelids. For example, the massaging action can be in small circular, angular, or up, down, left, and right motions across the exterior surface of the upper or lower eyelids. In operation, heat from the component piece 304 is applied to the eyelid to raise the temperature at the meibomian glands to the desired level. For example, heat may be applied to raise the temperature at the exterior of the eyelid to 102-108 degrees Fahrenheit, preferably 108 degrees Fahrenheit, or any temperature comfortable for the user or prescribed by a healthcare professional. It is contemplated within the scope of the invention that the Peltier device 212 can generate up to 120 degrees Fahrenheit with an approximate 12% drop in temperature as measured at the eyelid contact piece 304 with respect to the Peltier device 212.

Figure 22:
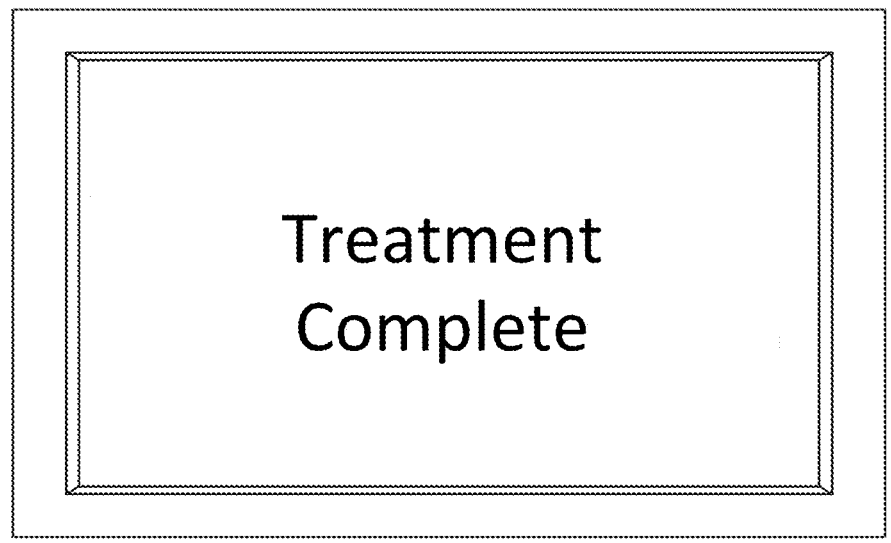

As previously mentioned, the heat from Peltier device 212 can be regulated, meaning that Peltier device 212 can be controlled to be within the desired programmed temperatures and programmed temperatures that are safe for the eyelid and at a sufficient temperature for melting, loosening, or softening an occlusion or obstruction in the meibomian gland. Further, the heat may be maintained in one or more areas of a single eyelid for a certain period of time and heat may be maintained for an entire treatment session, such as for 1-20 minutes, sufficient to raise the temperature at the meibomian glands sufficient to melt, loosen, or soften the obstructions or occlusions. Alternatively, and as previously mentioned, the timer 1408 can be pre-programmed by the user prior to a treatment session to indicate to the user when a session is complete. For example, the eye treatment device 100 can automatically turn off the Peltier 212 of hand piece 200 or device 100 altogether after a pre-set time has been reached. Alternatively, the timer may shut off while the Peltier 212 is still running until the main unit is manually shut-off. In addition, at the end of a session, the main unit 102 can generate an audible or visual indication. For example, the user interface screen can display 104 an end of session screen as shown in FIG. 22.

In an additional embodiment of the eye treatment device, the user may have one or more pre-programmed temperature and time profiles saved within the memory unit of device 100. For example, the user may need to use device 100 in multiple sessions depending on the severity of the MGD, such as over a course of multiple times during the day and/or multiple times during the course of a week, month, year, or multiple years. Regulated heat can include controlling heat according to a temperature profile saved with the memory unit of device 100. The temperature profile may be a constant temperature, or include ramp-ups, ramp-downs, peaks and valleys. Further, the temperature profile may include heat pulses or be modulated with various characteristics, including the use of on/off switching or pulse width modulation (PWM) techniques for example. The use of modulated heat may allow the temperature to be raised even higher at the eyelid without damages to the patient's eyelid since the increased temperatures are applied for shorter periods of time. Obstructions or occlusions in the meibomian glands may have melting, loosening, or softening points that are beyond temperatures that may be applied without the use of modulated heat. The temperature needed to melt, loosen, or soften obstructions or occlusions may depend on how keratinized the obstruction or occlusion is. Not all obstructions or occlusions have the same melting, loosening, or softening points. In other embodiments, a user, patient, or healthcare professional can also manually regulate the temperature in real-time on device 100 via user interface display 104, wherein display 104 shows the temperature of the peltier device 260 within hand piece 200. In other embodiments, device 100 can be wired or communicate wirelessly with a server, compute device, or mobile device. In other embodiments, the eye treatment device of the present invention is not intended to direct electrical signals to the eyelids. In addition, the eye treatment device of the present invention is not intrusive and does not lift the eyelids nor does it involve the eyelid applicator (or any other component) being positioned underneath the eyelids or treat the eyelids from underneath the eyelids.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes can be made with respect to various elements described herein without exceeding the scope of the invention. Although the present invention has been described in considerable detail with reference to certain preferred versions or embodiments thereof, other versions and embodiments are possible. For example, the present invention can also only comprise of a portable hand piece that is wireless and operates on battery and includes components such as a controller, display, and Peltier device without the need for main unit 102. For example, one or more components of main unit 102 can be integrated with a stand-alone and portable hand piece, similar to hand piece 200, for treating eye conditions. Therefore, the spirit and scope of the appended claims should not be limited to the description of the preferred versions contained herein.

What is claimed is:

1. An eye treatment device, comprising:
   a heating element; a thermal transfer rod;
   a first outer eyelid contact piece, wherein the first outer eyelid contact piece is further comprised of a rounded rectangular shape having a concave surface, wherein the concave surface further comprises a flat surface;
   a second outer eyelid contact piece, wherein the second outer eyelid contact piece is further comprised of a rounded rectangular shape having a concave surface, wherein the concave surface further comprises a flat surface;
   a gel substance;
   wherein the first and second outer eyelid contact pieces are coupled to the heating element via the thermal transfer rod, and wherein the first and second outer eyelid contact pieces are configured to directly apply heat to an exterior surface of an upper or lower eyelid via the gel substance;
   a controller in communication with the heating element, and wherein the controller is configured to regulate a temperature of the heating element; and
   wherein the thermal transfer rod is configured to transfer heat from the heating element to the first and second outer eyelid contact pieces via thermal conduction.

2. The eye treatment device of claim 1, wherein the heating element, thermal transfer rod, and first and second outer eyelid contact pieces are part of a hand-held unit.

3. The eye treatment device of claim 2, wherein the controller is disposed within a main unit independent of the hand-held unit.

4. The eye treatment device of claim 3, wherein the main unit communicates with the hand-held unit.

5. The eye treatment device of claim 3, wherein the main unit further comprises a graphical user interface comprising a digital timer for the heating element.

6. The eye treatment device of claim 1, wherein the heating element is disposed within a casing, and the thermal transfer rod is at least partially disposed within the casing.

7. The eye treatment device of claim 1, wherein the heating element is comprised of a Peltier device.

8. An eye treatment device, comprising:
   a heating element, wherein the heating element is comprised of a Peltier device adapted to generate temperatures up to 120 degrees Fahrenheit;
   a first end piece, wherein the first end piece is further comprised of a rounded rectangular shape, wherein an entire surface area of one side of the rounded rectangular shape is comprised of a flat concave configuration; and
   a second end piece, wherein the second end piece is further comprised of a rounded rectangular shape, wherein an entire surface area of one side of the rounded rectangular shape is comprised of a flat concave configuration;
   wherein the first and second end pieces are coupled to each other and further coupled to the heating element via a thermal transfer rod, and wherein the first and second end pieces are configured to directly apply heat to an exterior surface of one or more eyelids; and
   wherein the thermal transfer rod is configured to transfer heat from the heating element to the first and second end pieces via thermal conduction.

9. The eye treatment device of claim 8, wherein the temperature at the first and second end pieces ranges from 102 to 108 degrees Fahrenheit.

10. The eye treatment device of claim 8, wherein a temperature differential between the first and second end pieces and the heating element is approximately 12%.

11. The eye treatment device of claim 8, wherein the thermal transfer rod is bent approximately 30 degrees with respect to a horizontal plane.

12. The eye treatment device of claim 8, wherein the first and second end pieces and the thermal transfer rod form a T-shaped configuration.

13. The eye treatment device of claim 8, wherein the heating element is disposed within a casing and thermal transfer rod is coupled to the casing via a threaded engagement.

14. The eye treatment device of claim 8, further comprising an ultrasound gel substance.

15. An eye treatment device, comprising:
   a heating element;
   a thermal transfer rod;
   a first end piece, wherein the first end piece is comprised of a rounded rectangular shape having a concave surface;
   a second end piece, wherein the second end piece is comprised of a rounded rectangular shape having a concave surface;
   wherein the first and second end pieces are coupled to the heating element via the thermal transfer rod; and
   wherein the thermal transfer rod is configured to transfer heat from the heating element to the first and second end pieces via thermal conduction.

16. The eye treatment device of claim 15, wherein the thermal transfer rod is at an angle relative to a horizontal plane.

17. The eye treatment device of claim 15, wherein the first and second end pieces are comprised of silver.

18. The eye treatment device of claim 15, wherein the heating element is comprised of a thermoelectric or Peltier device, and wherein the thermal transfer rod is coupled to the thermoelectric or Peltier device.

19. The eye treatment device of claim 15, further comprising a controller having a graphical user interface configured to receive user input.

20. The eye treatment device of claim 15, further comprising a controller having a timer for operating the heating element.

* * * * *